(12) United States Patent
Vexler et al.

(10) Patent No.: US 6,168,572 B1
(45) Date of Patent: Jan. 2, 2001

(54) DEVICE FOR EXAMINING VISCOELASTICITY OF A LIVING OR ARTIFICIAL TISSUE

(75) Inventors: Akiva Vexler, Hod Hasharon; Raphael Gorodetsky, Jerusalem; Igor Polyansky, Bnev Aish, all of (IL)

(73) Assignee: Hadasit Medical Research Services & Development Company Ltd., Jerusalem (IL)

( * ) Notice: Under 35 U.S.C. 154(b), the term of this patent shall be extended for 0 days.

(21) Appl. No.: 09/101,739

(22) PCT Filed: Dec. 27, 1996

(86) PCT No.: PCT/IB96/01469
§ 371 Date: Jan. 8, 1999
§ 102(e) Date: Jan. 8, 1999

(87) PCT Pub. No.: WO97/25921
PCT Pub. Date: Jul. 24, 1997

(30) Foreign Application Priority Data
Jan. 16, 1996 (IL) .......... 116784

(51) Int. Cl.⁷ .......... A61B 5/103; A61B 5/117
(52) U.S. Cl. .......... 600/587
(58) Field of Search .......... 600/587; 128/774, 128/55, 660.02

(56) References Cited

U.S. PATENT DOCUMENTS

| | | | |
|---|---|---|---|
| 2,710,000 | * 6/1955 | Cromer et al. | 600/568 |
| 3,737,004 | 6/1973 | Higgs | 181/0.5 A |
| 4,396,025 | 8/1983 | De Rigal et al. | 128/774 |
| 4,947,851 | 8/1990 | Sarazyan et al. | 128/660.02 |
| 5,038,795 | 8/1991 | Roush et al. | 128/774 |
| 5,115,808 | 5/1992 | Popovic et al. | 128/660.02 |
| 5,408,882 | 4/1995 | McKinley et al. | 73/597 |

FOREIGN PATENT DOCUMENTS

| | | | |
|---|---|---|---|
| 0329817 | 8/1989 | (EP) | G01N 29/00 |
| 2079468 | 1/1982 | (GB) | G01N 3/00 |

OTHER PUBLICATIONS

O.A. Lindahl et al. :"Impression Techinque for the assessment of oedema: comparison with a new tactile sensor that measures physical property of tissue", *Medical and Biological Engineering and Computing*, vol. 33, No. 1, pp. 27–32, Jan. 1995.

* cited by examiner

Primary Examiner—Max Hindenburg
Assistant Examiner—Brian Szmal
(74) Attorney, Agent, or Firm—Davidson, Davidson & Kappel, LLC

(57) ABSTRACT

A probe for examining viscoelasticity and anisotrophy of an area of an external layer of a living or artificial tissue, comprises an assembly (34) including at least one group of piezoelectric spaced-apart transducers (78,80,82), each having a surface contact making edge, wherein one of said transducers operates as a transmitter and at least one other transducer operates as a receiver, and wherein said assembly is movable both axially, as well as angularly; means for effecting the controlled axial movement (22,24) of said assembly; means for controlling the contact pressure (24) to be exerted by the transducers on the surface of an area of a tissue to be examined, and means for effecting angular movement of said assembly (18,20) at a selected axial displacement.

16 Claims, 2 Drawing Sheets

DEVICE FOR EXAMINING VISCOELASTICITY OF A LIVING OR ARTIFICIAL TISSUE

The present invention relates to a device for examining the viscoelasticity and anisotropy of an area of an external surface of a living tissue, e.g., skin or artificial tissue.

The complex functions of the skin require maximum strength, as well as maximum flexibility. Many local or systemic lesions in the skin alter its structure and function. This may be reflected by significant changes in the mechanical properties of the affected skin area. Therefore, non-invasive assay of the mechanical properties of the skin such as hardness, stiffness and rigidity may be useful for monitoring skin disorders and lesions, as well as for the evaluation of skin changes relating to the physiological status of the individuals, in addition to their age, sex and race. So far, mostly subjective means are employed in clinical practice, including visual and palpating examinations of the skin lesion without discrete quantitative criteria. Histopathology, which may contribute more detailed information is invasive, complicated, expensive and needs special clinical skills, and moreover, by its nature is not repetitive or quantitative.

The relationship between the mechanical properties of viscoelastic matrices from different materials and the speed of propagation of shear surface waves (elastic waves) in the acoustic frequency range along the vector of the initial displacement of the material tested, was analyzed. According to the physical basis of the mechanics of elastic wave propagation, the speed of propagation of these waves in viscoelastic materials with constant mass density could be calculated from the expression:

$$v^2 = Y(1-m)/(1+m)(1-2m)p$$

where:
v=speed of propagation of longitudinal elastic surface shear wave;
Y=Young's modules of elasticity;
m=Poison coefficient of the material
p=Mass density of the material.

The viscoelastic properties of the material is characterized by one part of the equation:

$$Y(1-m)/(1+m)(1-2m) = \sigma$$

Consequently, the speed of propagation of elastic waves is proportional to the viscoelasticity of the material ($\sigma$=modules of elasticity) and its mass density is defined by:

$$v^2 = \sigma/p$$

Therefore, the measurement of the speed of elastic wave propagation allows the determination of the modules of elasticity of an external tissue examined by the expression:

$$\sigma = pv^2$$

Viscoelastic matrices with homogenous mechanical properties have isotropic modules of elasticity. Inhomogenous viscoelastic materials are characterized by the variations of the mechanical properties in different spatial orientations: this effect of anisotropy is exhibited by the modules of anisotropic elasticity. In the real biological tissues (for example, skin), the value of modules of elasticity in one direction can be several hundred percents greater than in the other direction.

A number of methods for the quantitative evaluation of the mechanical properties of tissues have been introduced but they have limited applications. These methods include identometry, uniaxial tensiometry, skin surface topography, torsion measurements, skin compliance to suction and others. A most promising approach for the evaluation of the mechanical properties of the viscoelastic materials is the measurement of the speed of propagation of elastic surface sheer waves (in acoustic frequency range) along the external tissues.

Accordingly, there is proposed a new multi-point probe and device for a non-invasive and safe measurement of the mechanical properties and anisotropy of an area of external layer of tissues. The device is based on the correlation between the tissue elasticity and the speed of propagation of a shear mechanical wave on its surface. The measurement is effected by a multi-directional (e.g., bi-directional) simultaneous examination of an array of points in the external tissue.

It is therefore a broad object of the present invention to provide a more advanced device for the measurement of the speed of propagation of elastic waves for the evaluation of the mechanical properties of living and artificial tissue for different applications.

The invention provides a probe for examining viscoelasticity and anisotropy of an area of an external layer of a living or artificial tissue, comprising an assembly including at least one group of piezoelectric spaced-apart transducers, each having a surface contact making edge, wherein one of said transducers operates as a transmitter and at least one other transducer operates as a receiver, and wherein said assembly is movable both axially, as well as angularly, means for effecting the controlled axial movement of said assembly, means for controlling the contact pressure to be exerted by the transducers on the surface of an area of a tissue to be examined, and means for effecting angular movement of said assembly at a selected axial displacement.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Figure 1:
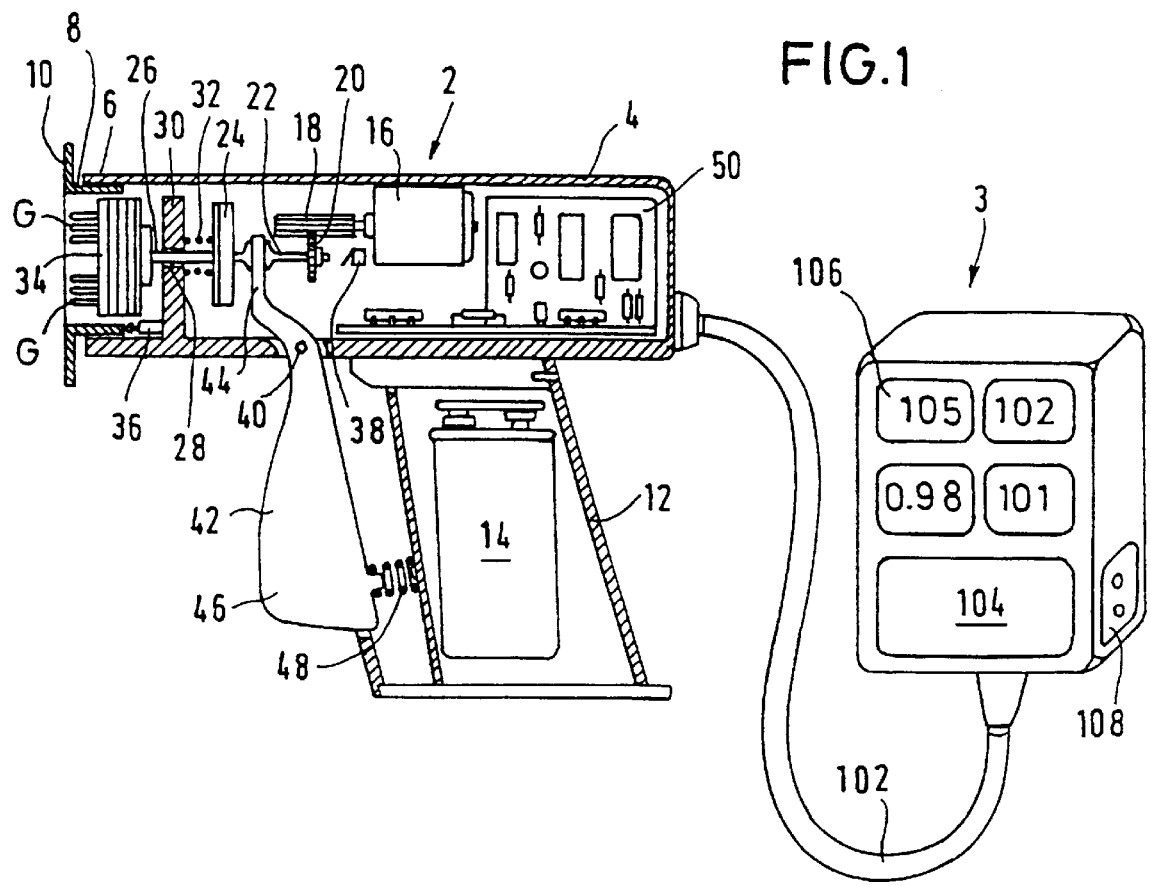
FIG. 1 is a cross-sectional view of a probe and a plan view of an electronic unit of the device according to the present invention.
Figure 2:
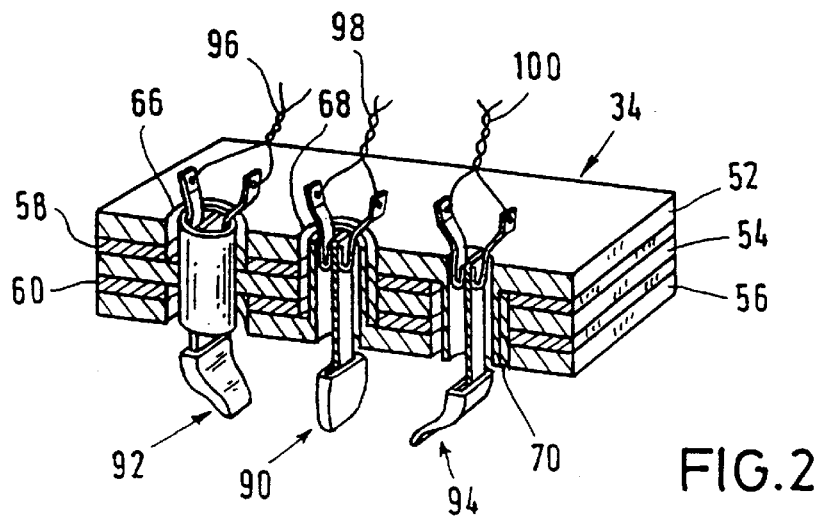
FIG. 2 is a cross-sectional view of a part of a movable assembly of the probe for mounting a multiplicity of transducers shown in FIG. 1.

In FIGS. 1 and 2, there is illustrated a device for examining the viscoelasticity and anisotropy of an area of a living or an artificial tissue consisting of a probe 2 and an electronic unit 3, by fast, non-invasive simultaneous multi-directional measurement of the mechanical properties of the tissue.

The probe 2, which is configured as a pistol consists of a housing 4 having an open end 6 engaging in a sliding fit, a tube 8 having a flange 10 and a hollow handle portion 12 forming a chamber for holding a battery 14. Further seen is a driver 16 actuating a revolving elongated gear 18 and a gear 20 engaged and driven by the elongated gear 18. To the gear 20 there is connected at one end thereof an axle 22, while the other end thereof is affixed to one side of a pressure control unit 24, e.g., a unit based on a Force Sensitive Resistor (FSR). To the other side of the pressure control unit there is attached a shaft 26, protruding through a hole 28 in a stationary partition 30 located inside the housing and a biasing spring 32 is disposed around a section of the shaft 26 and abuts both, the pressure control unit 24 and the partition 30. The other end of the shaft 26 is affixed to an assembly 34, the structure of which will be described hereinafter with reference to FIGS. 2 and 3. Interposed between the partition 30 and the inside end of the tube 8 is a switch 36 and a similar switch 38 is strategically affixed behind the gear 20. The functions of the switches will be described hereinafter. Pivotally attached to the housing about axis 40 is a trigger 42, the upper end portion 44 of which is coupled to the axle 22 for effecting its movement and the lower end portion 46 is fitted with a biasing spring 48. In the rear portion of the probe 2 is housed an electronic control unit 50.

Figure 3:
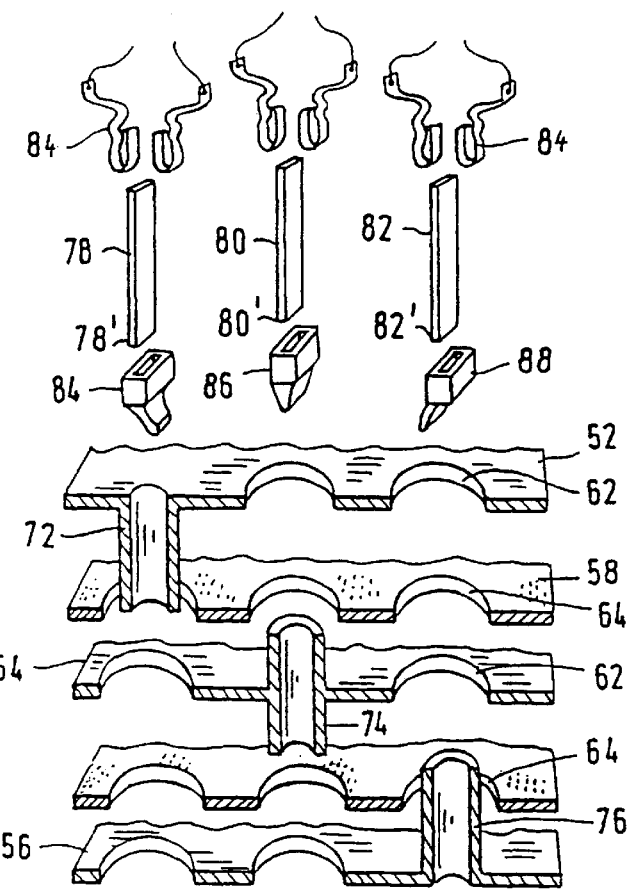
FIG. 3 is an exploded view of a part of the assembly shown in FIG. 2.

Referring to FIGS. 2 and 3 there is seen in greater detail the part of the assembly 34. The assembly 34 is advantageously composed of three rigid plates 52, 54, 56 made of an insulating material, e.g., plastic material, adhered by vibration dumping layers 58, 60 made of e.g., silicon rubber. As seen, each of the plates and layers are made with a plurality of holes 62, 64 so that when the plates and layers are aligned, there is formed in the assembly 34 throughgoing holes 66, 68, 70. The holes are lined with tubular sections 72, 74 and 76, wherein each section is integrally made with, or attached to one of the plates 52, 54 and 56, so as to mechanically separate the tubular sections from each other. The task of each of the thusly formed holes is to accommodate and retain piezoelectric transducers 78, 80 and 82. This is achieved by means of electrically conductive spring elements 84, suitably configured to squeeze a transducer in between two such elements, when inserted in the hollow of a tubular section (as seen in FIG. 2). The end portions 78', 80' and 82' of the piezoelectric transducers are advantageously fitted with tissue contact-making tips 84, 86 and 88, which insulate the surface of the tissue from electrical charges applied to the piezoelectric transducers and prevent electrical short-circuiting between the transmitter and receiver(s) through the tissue. The tips also serve to protect the piezoelectric transducers against chipping and breaking.

In addition, such tips, made, e.g., of plastic material, enable configuring the contact-making surfaces, so as to set the exact distance between them, e.g., the distance as measured between two lines, each having a minimal width, instead of the distance between the edges of the piezoelectric transducer elements, which may have a different shape.

In the preferred embodiment shown in the figures, there are provided four groups G of three such transducers, the middle transducer acting as a transmitter 90, with the transducers on both sides acting as receivers 92 and 94, all being electrically connected via wires 96, 98 and 100, respectively, to the electronic control unit 50 (FIG. 1). In general, there may be provided N groups of transducers, wherein each group G includes a transmitter and at least one spaced-apart receiver.

The electronic unit 3 is advantageously interconnected with the probe 2 by means of a cable 102 and essentially comprises a processor 104 and a display 106. In addition, the unit may be fitted with a communication port 108.

Figure 4:
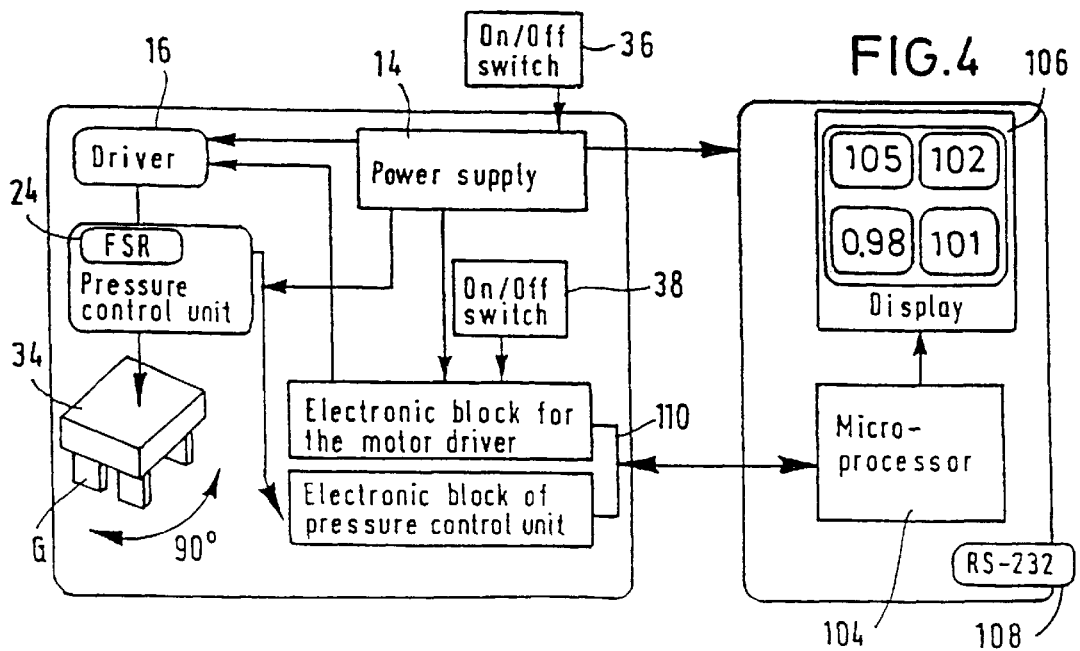
FIG. 4 is a block diagram of the device of FIG. 1.

Referring now also to FIG. 4, the operation of the device will be described. Upon the pressing of the probe 2 against an area of a tissue to be analyzed, the flange 10 of the tube 8 is displaced towards the inside of the probe, actuating the switch 36 which, in turn, turns on the power supply or battery 14. The measurements themselves commence only when the movable assembly 34 is pressed against the examined tissue area with a preset pressure. There are two ways to effect the axial displacement of the assembly 34: manually, by means of the trigger 42 and automatically, by means of a driver controlled by the processor 104. The manual mode of operation requires the actuation of the trigger 42 by pulling it, which actuation mechanically displaces the assembly 34 with respect to the flange 10. In the displaced state, the tips 84, 86 and 88 of the groups of the transducers coupled to the assembly, project beyond the plane of the flange 10 and press against the tissue to be analyzed until the desired contact pressure with the tissue is reached. The contact pressure is evaluated by the contact pressure control unit 24 and is continuously controlled by the electronic circuit 110. When the adequate pressure of the movable assembly 34 on the tissue is reached, the processor 104 initiates the measurements in a programmed sequence as follows: the processor 104 activates transmitter 90, which emits a tangential pulse inducing on the surface of the tissue a shear mechanical elastic wave in the acoustic frequency range. Only the waves propagating along the vector of the initial tissue displacement (directional waves or D-waves) are recorded. The time-of-flight of the D-wave from the transmitter 90 to one or each of the receivers 92 and 94 is used to evaluate the viscoelasticity of the examined tissue. The procedure is repeated for each of the groups G of the assembly. With the termination of the measurements in one direction across the tissue according to the orientation of the assembly, the trigger 42 is fully released while the probe 2 with the flanged tube 8 is still pressed against the examined tissue area. Upon the release of the trigger, the switch 38 is actuated by the displacement of the end portion of the axle 22. The actuation of the switch 38 through the electronic circuit 110, which controls the operation of the driver, causes the driver 16 to rotate the assembly 34 through any preset angle, e.g., through 90°, with all of the N groups G of the assembly. The measurement is then repeated pulling again on the trigger 42 until the desired pressure of the assembly on the surface of the tissue is regained, while the transducers are angularly realigned on the same points on the examining tissue area.

The information concerning the speed of a D-wave in at least two directions in all points on the tested area, is recorded and can also be displayed by the electronic unit 3. This feature of measuring each point in more than one direction enables the evaluation of anisotropy in viscoelasticity of the examined tissue. The accumulated measured and calculated data may then be unloaded and stored through port 108, in a personal or main frame computer for further detailed analysis and long term storage.

When, however, the axial displacement of the assembly 34 is effected automatically, the probe is equipped with an additional axial driving motor (not shown), receiving feedback signals from the pressure control unit 24 controlled by the processor 104. When the preset pressure of the movable assembly 34 applied to the examining tissue area is reached, the additional axial driving motor is switched off by the control circuit lo and the measurements are performed as described above. Upon the termination of the measurement in one direction, the processor 104 operates the axial motor driver to retreat the assembly 34. When the end portion of the axle 22 contacts switch 38, the angular motor driver 16 is turned on through the control circuit 110 to effect rotation of the assembly 34 through a preset rotation, e.g., through 90°. The axial motor driver is then re-operated and the assembly 34 is displaced outwardly until an adequate pressure on the surface of the tissue is achieved, whereupon an additional measurement is taken.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A probe for examining viscoelasticity and anisotropy in more than one direction of an area of an external layer of a living or artificial tissue, comprising:

an assembly including at least one group of piezoelectric spaced-apart transducers, each having a surface contact making edge, wherein one of said transducers operates as a transmitter and at least one other transducer operates as a receiver for measurements taken when said surface contact making edge of said transducers contact the surface of an area of the tissue to be examined, and wherein said assembly is movable both axially, as well as angularly;

means for effecting the controlled axial movement of said assembly to a position in which said surface contact making edges of said transducers contact said area of tissue and to a position in which said surface contact making edges of said transducers do not contact said area of tissue;

means for controlling the contact pressure to be exerted by the transducers on the surface of an area of tissue to be examined, and means for effecting angular movement of said assembly at a selected axial displacement at which said surface contact making edges of said transducers do not contact the surface of the tissue and thereby do not apply pressure on the tissue surface prior to taking a subsequent measurement on said tissue.

2. The probe as claimed in claim 1, wherein said assembly comprises at least three rigid plates adhered by silicone rubber layers acting as mechanical dampers.

3. The probe as claimed in claim 2, wherein said assembly is made with holes lined with tubular sections, each tubular section is connected to, or made integrally with, one of said rigid plates and housing a pair of contact-making electrical springs, each pair of springs supporting a piezoelectric transducer.

4. The probe as claimed in claim 1, wherein said group comprises a single transmitter flanked by two spaced-apart equidistant receivers.

5. The probe as claimed in claim 1, wherein each of said transducers are fitted at the contact-making edge with a tip made of electrical insulating material and configured to provide a predetermined accurate distance between the tips of said transmitter and a receiver.

6. The probe as claimed in claim 1, wherein said axial displacement of said assembly is effected by applying manual force.

7. The probe as claimed in claim 1, wherein said axial displacement of said assembly is effected by means of a motor-operated driver.

8. The probe as claimed in claim 1, wherein said means for effecting controlled axial movement of said assembly comprises a contact pressure control unit, based on a force sensitive resistor.

9. The probe as claimed in claim 1, wherein said means for effecting angular movement of said assembly is adapted to rotate the assembly at a preset angle.

10. The probe as claimed in claim 1, further comprising a processor and display unit interconnected therewith by means of a flexible electrical cable.

11. The probe as claimed in claim 1, wherein said probe is configured as a pistol, including a tubular housing portion having an open end and a gripping handle.

12. The probe as claimed in claim 11, wherein said assembly is disposed inside said tubular housing portion adjacent said open end.

13. The probe as claimed in claim 11, further comprising a flanged cylinder, telescopically engaging the housing's open end, and arranged to operate a switch upon the pressing thereof towards the interior of the tubular housing.

14. The probe as claimed in claim 11, wherein said switch operates the supply of electrical power from a power source.

15. The probe as claimed in claim 14, wherein a power source is disposed inside the gripping handle.

16. The probe as claimed in claim 11, further comprising a trigger for setting said assembly in an axial displacement, determining the pressure applied by said transducers on the surface of a tissue to be examined.

* * * * *